United States Patent
Shin et al.

(10) Patent No.: US 9,671,688 B2
(45) Date of Patent: Jun. 6, 2017

(54) MONOMER FOR HARDMASK COMPOSITION, HARDMASK COMPOSITION INCLUDING SAID MONOMER, AND METHOD FOR FORMING PATTERN USING SAID HARDMASK COMPOSITION

(71) Applicant: CHEIL INDUSTRIES INC., Gumi-si, Gyeongsangbuk-do (KR)

(72) Inventors: Seung-Wook Shin, Suwon-si (KR); Yun-Jun Kim, Suwon-si (KR); Hea-Jung Kim, Suwon-si (KR); Youn-Jin Cho, Suwon-si (KR); Yoo-Jeong Choi, Suwon-si (KR)

(73) Assignee: Cheil Industries, Inc., Gumi-Si, Gyeongsangbuk-do (KR)

( * ) Notice: Subject to any disclaimer, the term of this patent is extended or adjusted under 35 U.S.C. 154(b) by 0 days.

(21) Appl. No.: 14/441,338

(22) PCT Filed: Oct. 2, 2013

(86) PCT No.: PCT/KR2013/008836
§ 371 (c)(1),
(2) Date: May 7, 2015

(87) PCT Pub. No.: WO2014/104544
PCT Pub. Date: Jul. 3, 2014

(65) Prior Publication Data
US 2015/0301446 A1 Oct. 22, 2015

(30) Foreign Application Priority Data

Dec. 28, 2012 (KR) .................. 10-2012-0157570

(51) Int. Cl.
| | | |
|---|---|---|
| *G03F 7/004* | (2006.01) | |
| *G03F 7/09* | (2006.01) | |
| *G03F 7/11* | (2006.01) | |
| *G03F 7/26* | (2006.01) | |
| *G03F 7/30* | (2006.01) | |
| *G03F 7/40* | (2006.01) | |
| *G03F 7/16* | (2006.01) | |
| *G03F 7/36* | (2006.01) | |
| *C07C 65/34* | (2006.01) | |
| *C07C 65/32* | (2006.01) | |
| *C07C 65/40* | (2006.01) | |
| *C07C 63/15* | (2006.01) | |
| *C07C 63/26* | (2006.01) | |
| *G03F 1/00* | (2012.01) | |

(52) U.S. Cl.
CPC .............. *G03F 7/004* (2013.01); *C07C 63/15* (2013.01); *C07C 63/26* (2013.01); *C07C 65/32* (2013.01); *C07C 65/34* (2013.01); *C07C 65/40* (2013.01); *G03F 1/00* (2013.01); *G03F 7/09* (2013.01); *G03F 7/091* (2013.01); *G03F 7/094* (2013.01); *G03F 7/11* (2013.01); *G03F 7/162* (2013.01); *G03F 7/26* (2013.01); *G03F 7/30* (2013.01); *G03F 7/36* (2013.01); *G03F 7/40* (2013.01)

(58) Field of Classification Search
None
See application file for complete search history.

(56) References Cited

U.S. PATENT DOCUMENTS

| | | | | |
|---|---|---|---|---|
| 6,903,131 B2 * | 6/2005 | Taveras | ............... | C07D 207/456 514/422 |
| 2007/0060596 A1 * | 3/2007 | Giblin | ................... | C04B 35/632 514/259.31 |
| 2007/0264828 A1 | 11/2007 | Jung | | |
| 2009/0264653 A1 * | 10/2009 | Bartolini | ............... | C07D 209/30 544/238 |
| 2010/0291483 A1 * | 11/2010 | Hamada | .................... | G03F 7/11 430/282.1 |
| 2012/0129831 A1 * | 5/2012 | Heimbach | ............ | C07D 413/14 514/210.18 |

FOREIGN PATENT DOCUMENTS

| | | |
|---|---|---|
| CN | 102540729 A | 7/2012 |
| JP | 2-248951 | * 10/1990 |

(Continued)

OTHER PUBLICATIONS

Boggiano et al ("Four Higher Annellated Pyrenes with Acene Character", Journal of the Chemical Society (1957), p. 2681-2689).*

(Continued)

*Primary Examiner* — Sin Lee
(74) *Attorney, Agent, or Firm* — Lee & Morse, P.C.

(57) ABSTRACT

Disclosed are a monomer represented by the following Chemical Formula 1 for a hardmask composition, a hardmask composition including the monomer, and a method of forming patterns using the same.

[Chemical Formula 1]

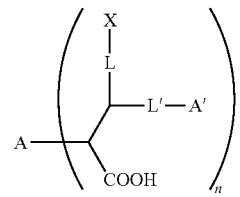

In the above Chemical Formula 1, A, A', L, L', X and n are the same as defined in the specification.

12 Claims, No Drawings

(56) References Cited

FOREIGN PATENT DOCUMENTS

| JP | 4-225982 | * | 8/1992 |
|---|---|---|---|
| JP | 2000-169424 | * | 6/2000 |
| JP | 2006-053404 A | | 2/2006 |
| KR | 10-2008-0107208 A | | 12/2008 |
| KR | 10-2009-0058528 A | | 6/2009 |
| KR | 10-2010-0062629 A | | 6/2010 |
| KR | 10-2010-0080147 A | | 7/2010 |
| KR | 10-2011-0079201 A | | 7/2011 |
| KR | 10-2012-0068378 A | | 6/2012 |
| KR | 10-2012-0068379 A | | 6/2012 |
| KR | 10-2012-0073817 A | | 7/2012 |
| KR | 10-2012-0077466 A | | 7/2012 |

OTHER PUBLICATIONS

Chemical Abstract (Accession No. 2000:412203) for JP2000-169424 (2000).*
Derwent English abstract for JP2-248951 (1990).*
Xu et al (Chemical Abstract (Accession No. 2004:396530) for "Isolation and Characterization of Fluoro-Jade B, a Selective Histochemical Stain for Neuronal Degeneration", Journal of Liquid Chromatography & Related Technologies (2004), 27(10), p. 1627-1640).*
Diesbach et al (Chemical Abstract (Accession No. 1942:33178) for "1,4-Dialdehydo-2,5-benzenedicarboxylic and 1,3-dialdehydo-4,6-benzenedicarboxylic acids", Helvetica Chimica Acta (1941), 24, p. 1306-16).*
Weizmann et al (Chemical Abstract (Accession No. 1939:29842) for "Boric acid synthesis of peri-hydroxyanthraquinones", Journal of the Chemical Society (1939), p. 398-401).*
Derwent English abstract for JP 4-225982 (1992).*
Boggiano, et al., "519. Four Higher Annelated Pyrenes with Acene Character", J. Chem. Soc., 1957, 2681-2689.
Taiwanese Search Report dated Sep. 26, 2014 in Corresponding Taiwanese Patent Application No. 102145484.

* cited by examiner

MONOMER FOR HARDMASK COMPOSITION, HARDMASK COMPOSITION INCLUDING SAID MONOMER, AND METHOD FOR FORMING PATTERN USING SAID HARDMASK COMPOSITION

TECHNICAL FIELD

A monomer for a hardmask composition, a hardmask composition including the monomer, and a method of forming a pattern using the hardmask composition are disclosed.

BACKGROUND ART

Recently, the semiconductor industry has developed an ultra-fine technique having a pattern of several to several tens of nanometers in size. Such ultrafine technique essentially needs effective lithographic techniques.

The typical lithographic technique includes providing a material layer on a semiconductor substrate; coating a photoresist layer thereon; exposing and developing the same to provide a photoresist pattern; and etching the material layer using the photoresist pattern as a mask.

Nowadays, when small-sizing the pattern to be formed, it is difficult to provide a fine pattern having an excellent profile by only the above-mentioned typical lithographic technique. Accordingly, a layer, called a hardmask layer, may be formed between the material layer and the photoresist layer to provide a fine pattern.

The hardmask layer plays the role of an intermediate layer for transferring the fine pattern of photoresist to the material layer through a selective etching process. Accordingly, the hardmask layer is required to have characteristics such as heat resistance and etch resistance, and the like during the multiple etching processes.

On the other hand, it has been recently suggested to form a hardmask layer by a spin-on coating method instead of chemical vapor deposition. The spin-on coating method requires a hardmask composition having dissolubility for a solvent.

The dissolubility is related to gap-filling characteristics for filling a hardmask composition in gaps between patterns, as well as planarization characteristics. As the molecular weight of a monomer for a hardmask composition becomes lower, the gap-filling characteristics become better.

However, when the monomer for the hardmask composition has a molecular weight, out-gas may be generated during a high temperature process.

DISCLOSURE

Technical Problem

One embodiment provides a monomer for a hardmask composition having excellent chemical resistance and etch resistance without generating out-gas.

Another embodiment provides a hardmask composition including the monomer.

Yet another embodiment provides a method of forming patterns using the hardmask composition.

Technical Solution

According to one embodiment, a monomer for a hardmask composition represented by the following Chemical Formula 1 is provided.

[Chemical Formula 1]

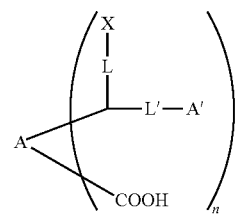

In the above Chemical Formula 1,

A and A' are each independently a substituted or unsubstituted C6 to C60 aromatic cyclic group, a substituted or unsubstituted C5 to C60 aliphatic cyclic group, a substituted or unsubstituted C2 to C60 hetero aromatic cyclic group, a substituted or unsubstituted C2 to C60 hetero aliphatic cyclic group, or a combination thereof, X is a hydrogen atom, an oxygen atom, a halogen atom, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, L is a single bond or a double bond, L' is a single bond or a substituted or unsubstituted C1 to C6 alkylene group, and n is an integer ranging from 1 to 3.

When X is an oxygen atom, L is a double bond. When X is hydrogen, a halogen atom, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, L is a single bond.

A may be derived from an acid anhydride compound selected from the following Group 1.
[Group 1]

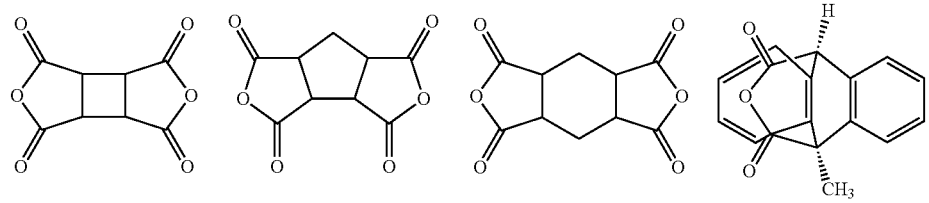

-continued
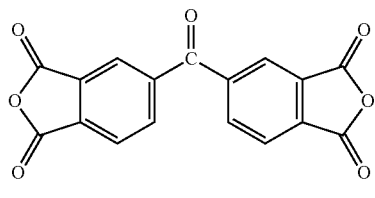
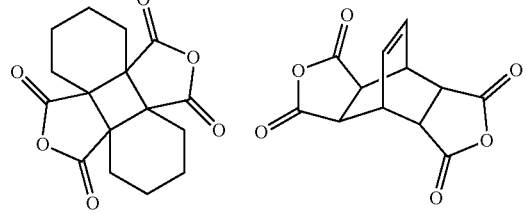
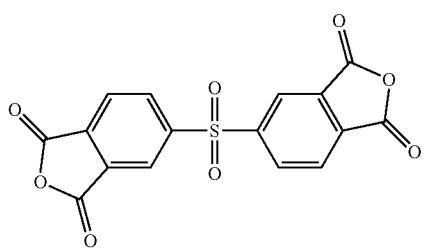
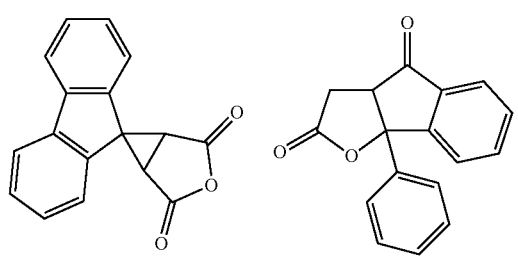
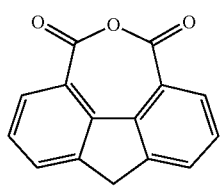
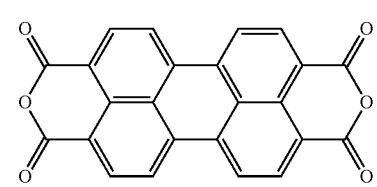
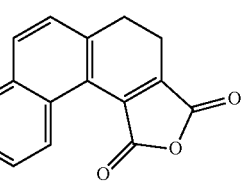
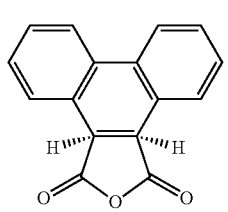
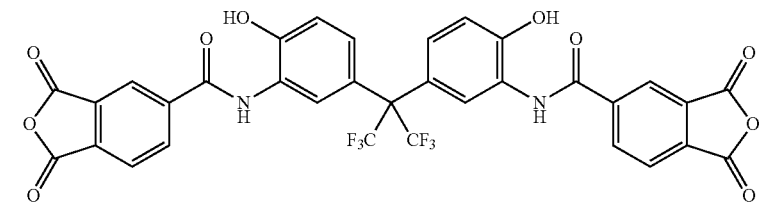
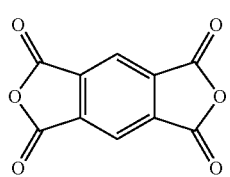
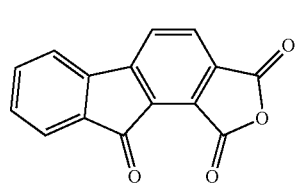
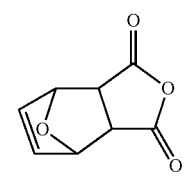
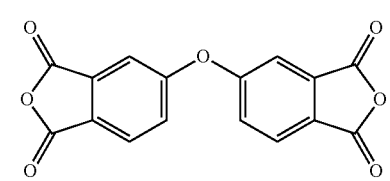
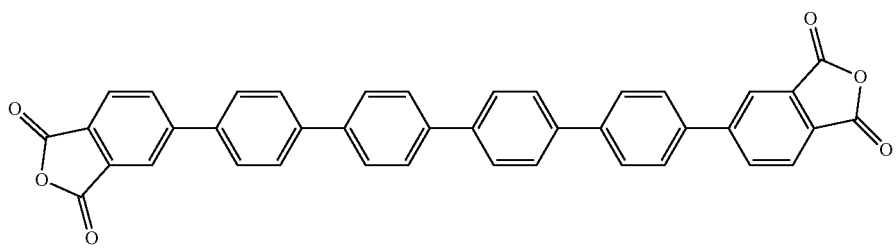
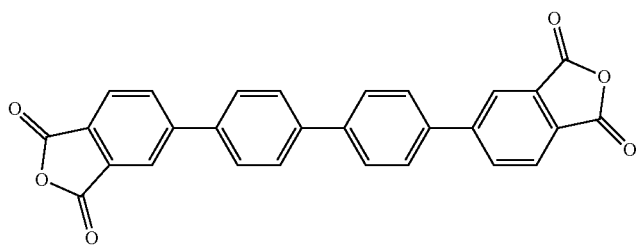

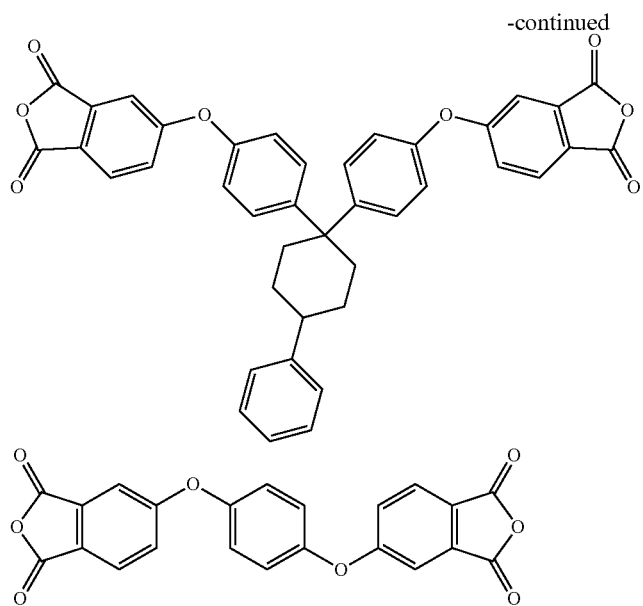

In the above Chemical Formula 1, A and A' are each independently a substituted or unsubstituted benzene group, a substituted or unsubstituted naphthalene group, a substituted or unsubstituted biphenyl group, a substituted or unsubstituted pyrene group, a substituted or unsubstituted perylene group, a substituted or unsubstituted benzoperylene group, a substituted or unsubstituted coronene group, or a combination thereof.

In the above Chemical Formula 1, at least one hydrogen of A' may be substituted with a hydroxy group.

In the above Chemical Formula 1, the monomer may be represented by the following Chemical Formula 1-1, 1-2, or 1-3.

[Chemical Formula 1-1]

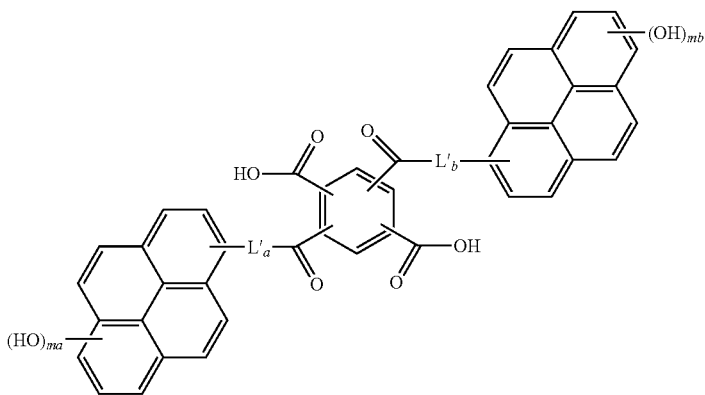

[Chemical Formula 1-2]

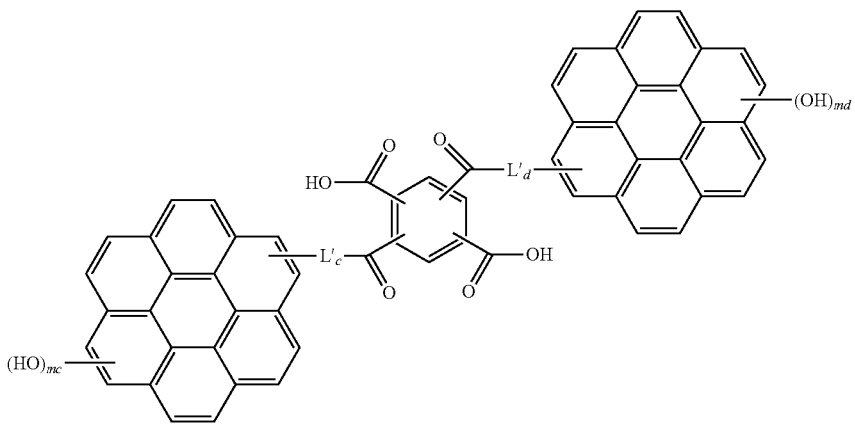

-continued

[Chemical Formula 1-3]

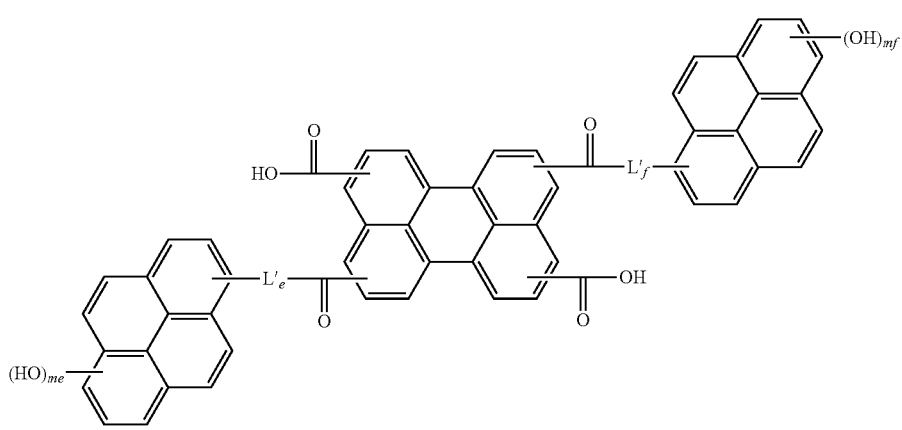

In the above Chemical Formulae 1-1, 1-2, and 1-3, $L'_a$, $L'_b$, $L'_c$, $L'_d$, $L'_e$, and $L'_f$ are each independently a single bond or a substituted or unsubstituted C1 to C6 alkylene group, ma, mb, me, and mf are each independently an integer of 0 to 9, and mc and md are each independently an integer of 0 to 11.

The ma, mb, mc, md, me, and mf indicate the number of a substituted hydroxy group.

The monomer for a hardmask composition may be represented by the following Chemical Formula 1-1a, 1-1b, 1-2a, 1-2b, or 1-3a.

[Chemical Formula 1-1a]

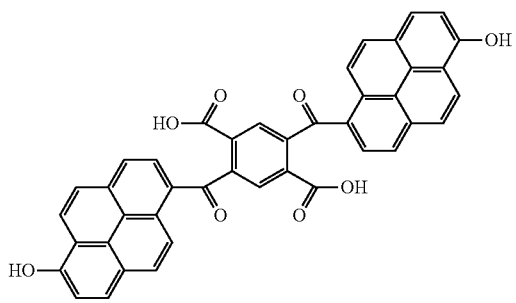

[Chemical Formula 1-1b]

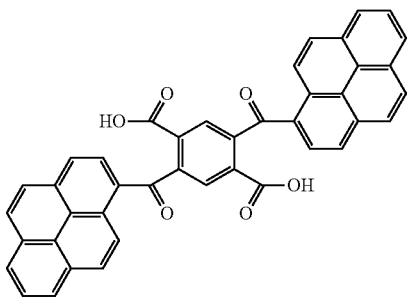

[Chemical Formula 1-2a]

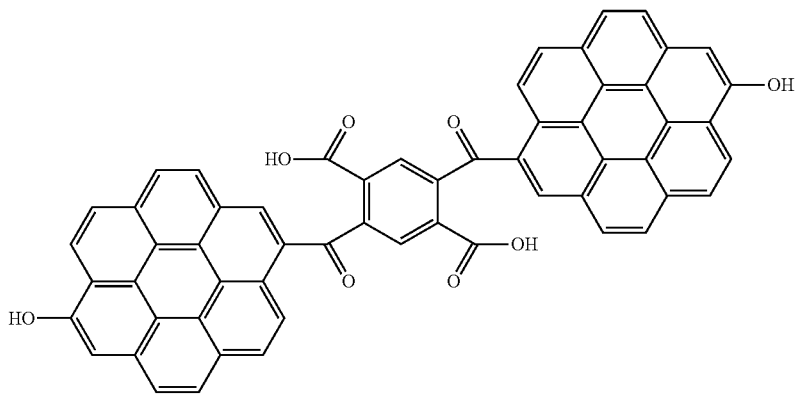

-continued

[Chemical Formula 1-2b]

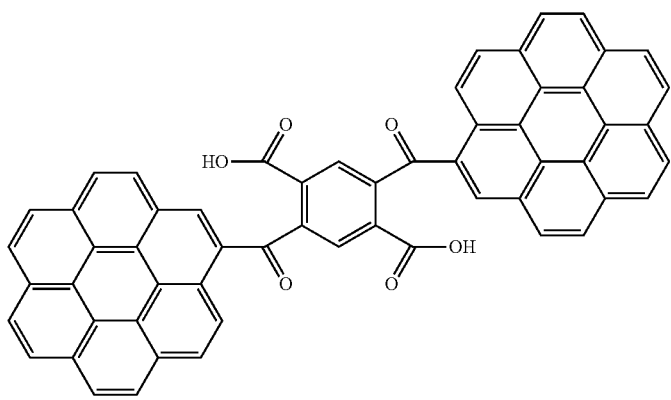

[Chemical Formula 1-3a]

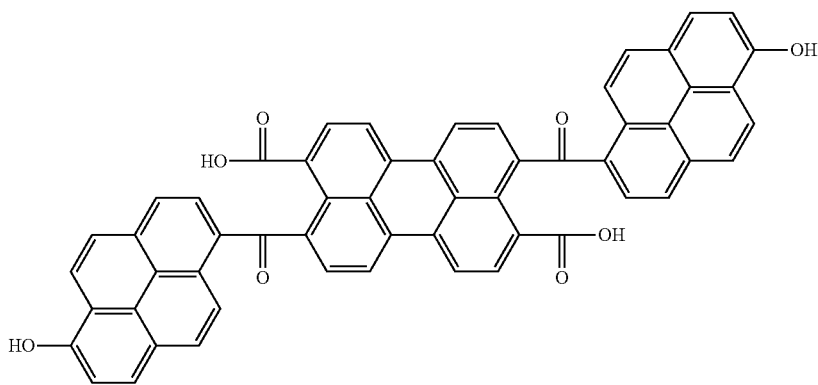

The monomer for a hardmask composition may have a molecular weight of 300 to 3,000.

According to another embodiment, a hardmask composition including the monomer and a solvent is provided.

The monomer may be included in an amount of 1 wt % to 30 wt % based on the total amount of the hardmask composition.

According to another embodiment, a method of forming patterns includes providing a material layer on a substrate, applying the hardmask composition on the material layer using a spin-on coating method, heat-treating the hardmask composition at 100° C. to 500° C. to form a hardmask layer, forming a silicon-containing thin film on the hardmask layer, forming a photoresist layer on the silicon-containing thin film, exposing and developing the photoresist layer to form a photoresist pattern, selectively removing the silicon-containing thin film and the hardmask layer using the photoresist pattern to expose a part of the material layer, and etching an exposed part of the material layer.

The hardmask composition may be applied using a spin-on coating method.

The process of forming a hardmask layer may include heat-treating at about 100° C. to 500° C.

Advantageous Effects

According to one embodiment, excellent optical properties may be secured while obtaining satisfactory dissolubility for a solvent, gap-fill characteristics, and planarization characteristics.

BEST MODE

Exemplary embodiments of the present invention will hereinafter be described in detail, and may be easily performed by those who have common knowledge in the related art. However, this disclosure may be embodied in many different forms and is not construed as limited to the exemplary embodiments set forth herein.

In the present specification, when a definition is not otherwise provided, 'substituted' refers to one substituted with at least a substituent selected from a halogen atom (F, Cl, Br, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C4 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C30 heterocycloalkyl group, or a combination thereof, instead of hydrogen of a compound.

In the present specification, when a definition is not otherwise provided, 'hetero' refers to one including 1 to 3 heteroatoms selected from N, O, S, or P.

Hereinafter, a monomer for a hardmask composition according to one embodiment is described.

A hardmask composition may be represented by the following Chemical Formula 1.

[Chemical Formula 1]

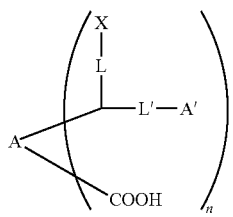

In the above Chemical Formula 1, definitions of A, A', L, L', X, and n are as follows.

A and A' are each independently a substituted or unsubstituted C6 to C60 aromatic cyclic group, a substituted or unsubstituted C5 to C60 aliphatic cyclic group, a substituted or unsubstituted C2 to C60 hetero aromatic cyclic group, a substituted or unsubstituted C2 to C60 hetero aliphatic cyclic group, or a combination thereof, X is a hydrogen atom, an oxygen atom, a halogen atom, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, L is a single bond or a double bond, L' is a single bond or a substituted or unsubstituted C1 to C6 alkylene group, and n is an integer ranging from 1 to 3.

When X is an oxygen atom, L is a double bond. When X is hydrogen, a halogen atom, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, L is a single bond.

In the above Chemical Formula 1, substituents linked with A and A' do not substitute with a particular ring of A and A' but may be substituted with hydrogen of all the rings of A and A'.

The monomer includes an aromatic or aliphatic cyclic group for a core moiety and at least one aromatic or aliphatic cyclic group for a substituent moiety and thus, may have rigid characteristics.

The monomer structurally has a carboxyl group for a substituent. The carboxyl group releases acid and promotes a cross-linking reaction and thus, may amplify cross-linking of the monomer for a short time and realize excellent cross-linking characteristics.

Accordingly, the monomer is cross-linked into a polymer for a short time despite heat treatment at a relatively low temperature and may realize excellent mechanical characteristics, heat resistance characteristics, chemical resistance, and etch resistance required of a hardmask layer.

In particular, the monomer has a relatively low molecular weight but the aforementioned structure may realize excellent cross-linking characteristics and thus generate no outgas.

The core moiety may be derived from an acid anhydride compound selected from the following Group 1.

[Group 1]

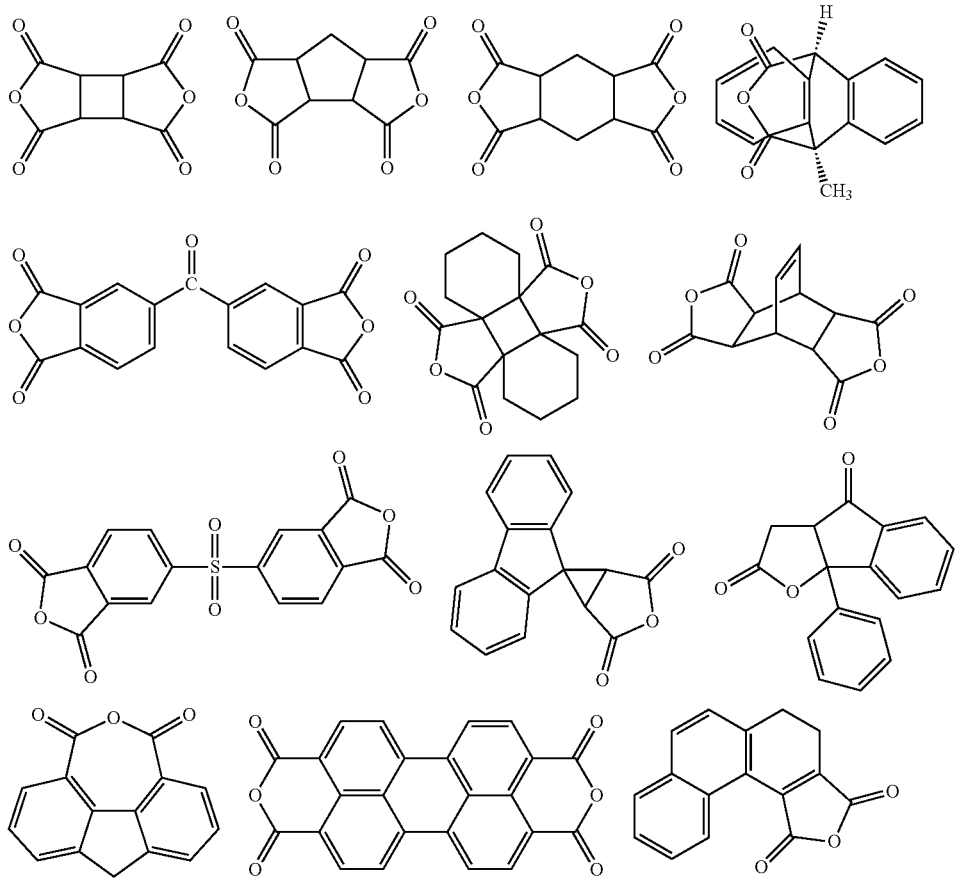

-continued

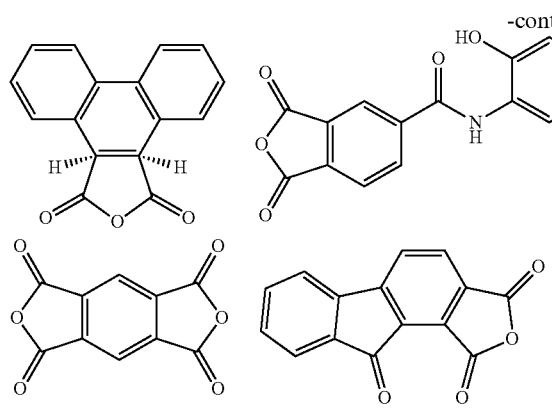
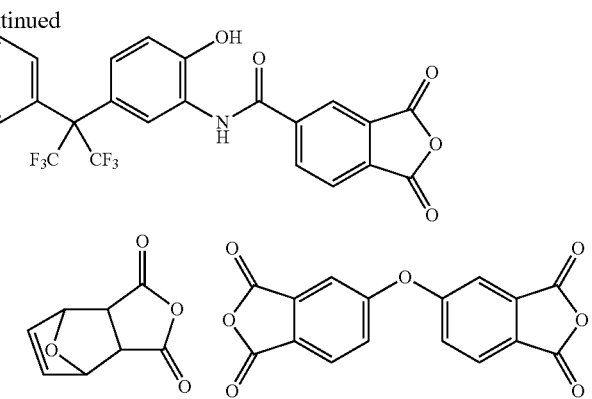
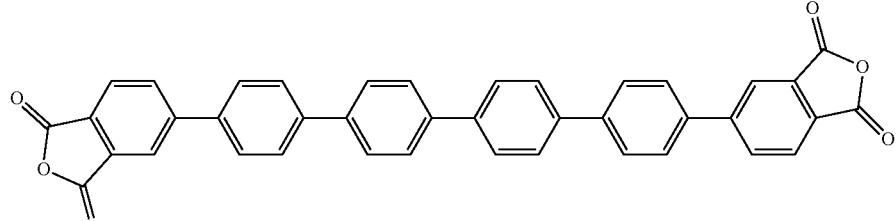
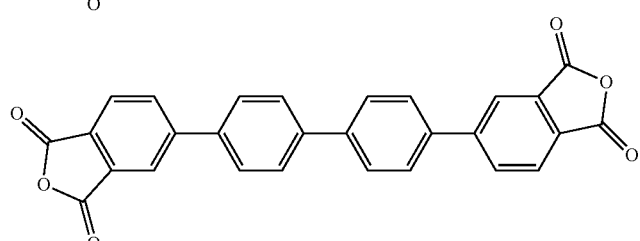
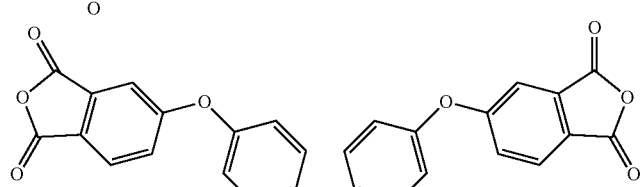
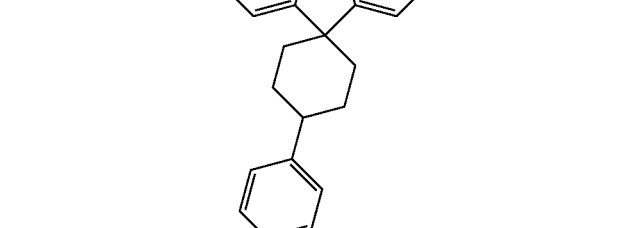
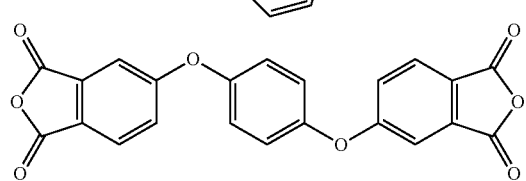

The core moiety may be a substituted or unsubstituted benzene group, a substituted or unsubstituted naphthalene group, a substituted or unsubstituted biphenyl group, a substituted or unsubstituted pyrene group, a substituted or unsubstituted perylene group, a substituted or unsubstituted benzoperylene group, a substituted or unsubstituted coronene group, or a combination thereof.

The substituent moiety may include a substituted or unsubstituted benzene group, a substituted or unsubstituted naphthalene group, a substituted or unsubstituted biphenyl group, a substituted or unsubstituted pyrene group, a substituted or unsubstituted perylene group, a substituted or unsubstituted benzoperylene group, a substituted or unsubstituted coronene group, or a combination thereof.

In addition, the aromatic or aliphatic cyclic group positioned in the substituent moiety of the monomer may include at least one hydroxy group. Accordingly, the monomer also has high dissolubility for a solvent as well as excellent cross-linking characteristics and thus, may be prepared into a solution, so that the solution may be spin-on-coated.

In addition, the monomer also has excellent gap-filling and planarization characteristics of filling a gap among patterns, when spin coated on a lower layer having a predetermined pattern.

X of the monomer is a hydrogen atom, an oxygen atom, a halogen atom, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group.

When X is an oxygen atom, and L is a double bond. When X is hydrogen, a halogen atom, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, and L is a single bond.

The monomer may be, for example represented by the following Chemical Formula 1-1, 1-2, or 1-3.

[Chemical Formula 1-1]

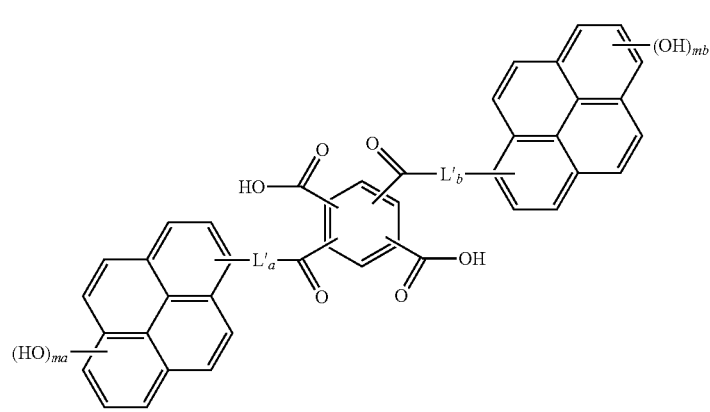

[Chemical Formula 1-2]

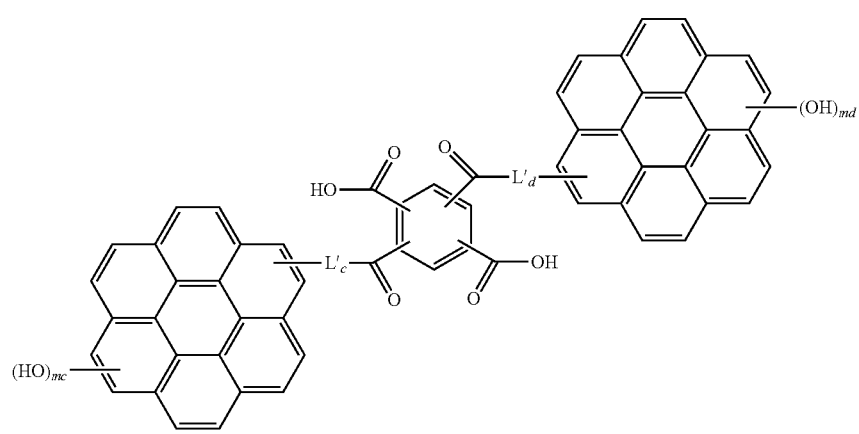

[Chemical Formula 1-3]

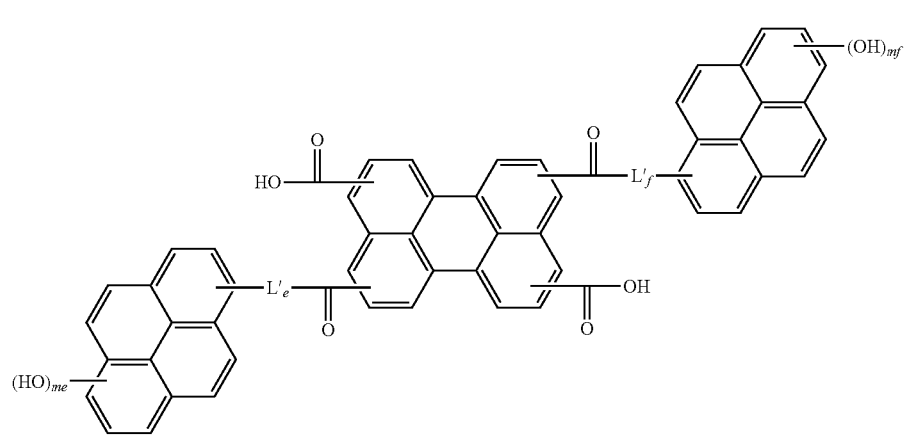

In the above Chemical Formulae 1-1, 1-2, and 1-3,

L'a, L'b, L'c, L'd, L'e, and L'f are each independently a single bond or a substituted or unsubstituted C1 to C6 alkylene group, ma, mb, me, and mf are each independently an integer of 0 to 9, and mc and md are each independently an integer of 0 to 11.

In particular, ma, mb, mc, md, me, and mf indicate the number of a substituted hydroxy group.

The monomer for a hardmask composition may be represented by the following Chemical Formula 1-1a, 1-1b, 1-2a, 1-2b, or 1-3a.

[Chemical Formula 1-1a]

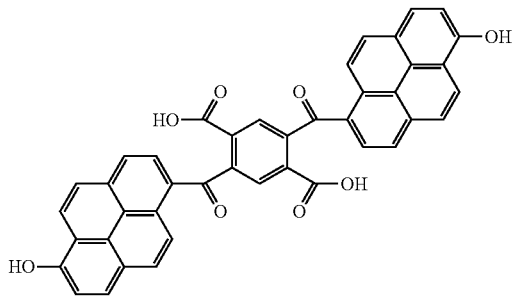

[Chemical Formula 1-1b]

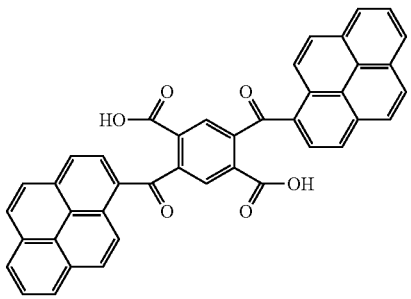

[Chemical Formula 1-2a]

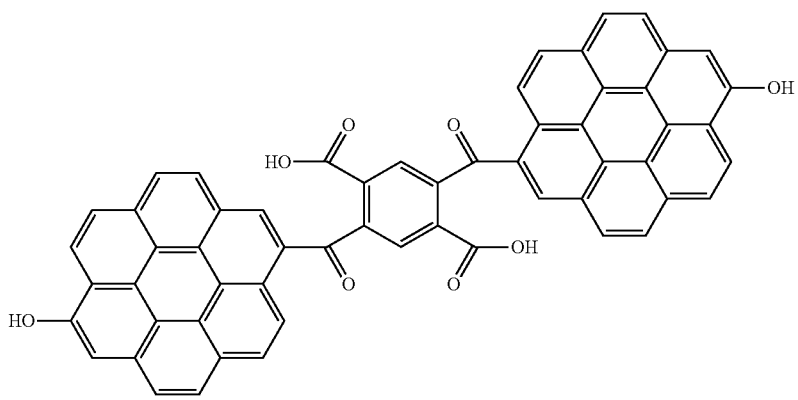

[Chemical Formula 1-2b]

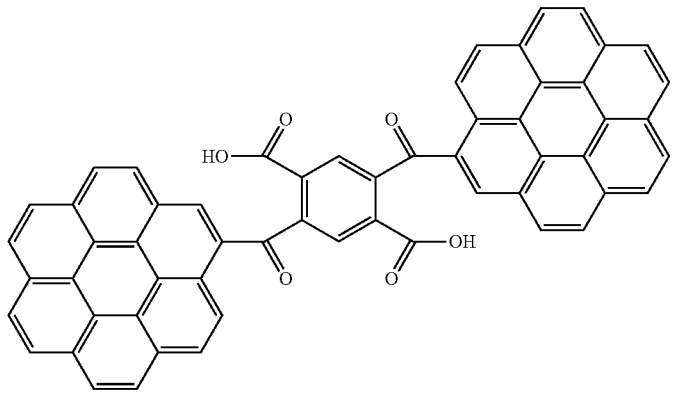

[Chemical Formula 1-3a]

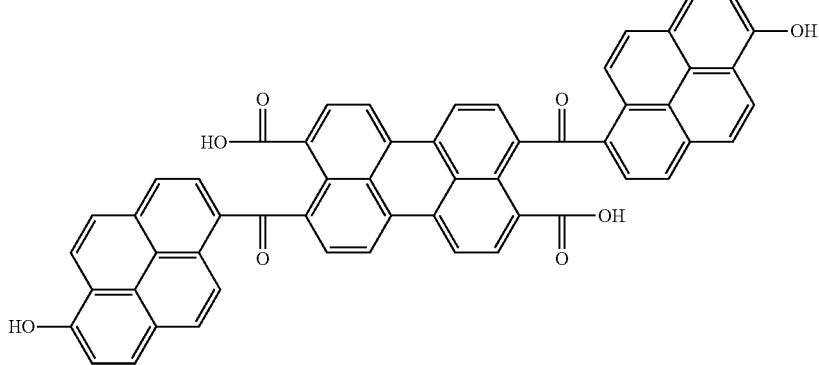

The monomer for a hardmask composition may have a molecular weight of 300 to 3,000. When the monomer has a molecular weight within the above range, solubility of the monomer having a high carbon content for a solvent is improved and an improved thin layer may be obtained through spin coating.

Hereinafter, a hardmask composition according to one embodiment is described.

A hardmask composition according to one embodiment includes the monomer and a solvent.

The monomer is the same as described above, and one kind of monomer may be used singularly and two or more kinds of monomers may be mixed.

The solvent may be anyone having sufficient dissolubility or dispersion for the monomer and may be, for example at least one selected from propylene glycol, propylene glycol diacetate, methoxy propanediol, diethylene glycol, diethylene glycol butylether, tri(ethyleneglycol)monomethylether, propylene glycol monomethylether, propylene glycol monomethylether acetate, cyclohexanone, ethyllactate, gamma-butyrolactone, methylpyrrolidone, acetylacetone, or ethyl 3-ethoxypropionate.

The monomer may be included in an amount of about 1 to 30 wt % based on the total amount of the hardmask composition. When the monomer is included in the above range, a desired thickness of a coated thin film may be obtained.

The hardmask composition may further include a surfactant.

The surfactant may include, for example, alkylbenzene sulfonate salt, alkyl pyridinium salt, polyethylene glycol, or a quaternary ammonium salt, but is not limited thereto.

The surfactant may be included in an amount of about 0.001 to 3 parts by weight based on 100 parts by weight of the hardmask composition. Within the amount range, the solubility may be secured without changing the optical properties of the hardmask composition.

Hereafter, a method for forming patterns by using the hardmask composition is described.

A method of forming patterns according to one embodiment includes providing a material layer on a substrate, applying the hardmask composition including the monomer and solvent on the material layer, heat-treating the hardmask composition to form a hardmask layer, forming a silicon-containing thin film on the hardmask layer, forming a photoresist layer on the silicon-containing thin film, exposing and developing the photoresist layer to form a photoresist pattern, selectively removing the silicon-containing thin film and the hardmask layer using the photoresist pattern to expose a part of the material layer, and etching an exposed part of the material layer.

The substrate may be, for example, a silicon wafer, a glass substrate, or a polymer substrate.

The material layer is a material to be finally patterned, for example a metal layer such as an aluminum layer and a copper layer, a semiconductor layer such as a silicon layer, or an insulation layer such as a silicon oxide layer and a silicon nitride layer. The material layer may be formed through a method such as a chemical vapor deposition (CVD) process.

The hardmask composition may be applied by spin coating in the form of a solution. Herein, the thickness of the hardmask composition is not particularly limited, but may be, for example about 100 Å to about 50,000 Å.

The heat-treating the hardmask composition may be performed, for example at about 100° C. to 500° C. for about 10 seconds to 10 minutes. During heat-treating, the monomer may cause a self cross-linking and/or mutual cross-linking reaction.

An auxiliary layer may be further formed on the hardmask layer. Herein, the auxiliary layer may be a silicon-containing thin film, which may be made of for example silicon nitride or silicon oxide.

A bottom anti-reflective coating (BARC) may be further formed on the auxiliary layer of the silicon-containing thin film.

Exposure of the photoresist layer may be performed using, for example ArF, KrF, or EUV. After exposure, heat treatment may be performed at about 100° C. to 500° C.

The etching process of the exposed part of the material layer may be performed through a dry etching process using an etching gas and the etching gas may be, for example $CHF_3$, $CF_4$, $Cl_2$, $BCl_3$, or a mixed gas thereof.

The etched material layer may be formed in a plurality of patterns, and the plurality of patterns may be metal patterns, semiconductor patterns, insulation patterns, or the like, for example diverse patterns of a semiconductor integrated circuit device.

Hereinafter, the present disclosure is illustrated in more detail with reference to examples. However, these examples are exemplary, and the present disclosure is not limited thereto.

Mode for Invention

Synthesis of Monomer

Synthesis Example 1

First Step: Coupling Reaction (Friedel-Craft Acylation)

4.7 g of pyromellitic dianhydride, 10.0 g of 1-methoxy-pyrene, and 287 g of 1,2-dichloroethane were put in a flask and agitated. 17.22 g of aluminum chloride was slowly added to the solution, and the mixture was heated and agitated at 60° C. for 12 hours. When the reaction was complete, the reactant was added to methanol in a dropwise fashion, and a precipitate produced therein was filtered and dried.

Second Step: Demethylation Reaction 10.00 g of the compound obtained in the first step, 14.82 g of 1-dodecanethiol, 4.93 g of potassium hydroxide, and 69.43 g of N,N-dimethylformamide were put in a flask and agitated at 110° C. for 8 hours. The reactant was cooled down and neutralized into a pH of about 6-7 by using a 5% hydrogen chloride solution, and a precipitate produced therein was filtered and dried, obtaining a monomer represented by the following Chemical Formula 1-1a.

[Chemical Formula 1-1a]

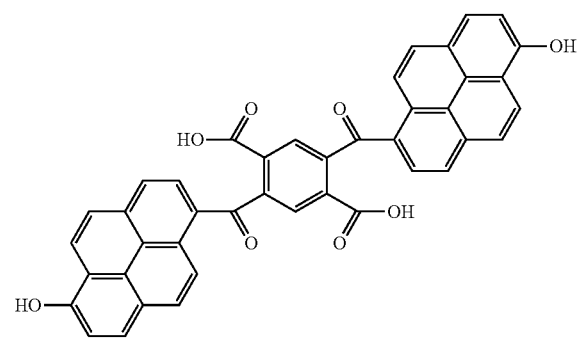

Synthesis Example 2

Coupling Reaction (Friedel-Craft Acylation)

5.4 g of pyromellitic dianhydride, 10.0 g of pyrene, and 316.8 g of 1,2-dichloroethane were put in a flask and agitated. 19.8 g of aluminum chloride was slowly added to the solution, and the mixture was heated and agitated at 60° C. for 12 hours. When the reaction was complete, a precipitate obtained by adding methanol to the reactant in a dropwise fashion was filtered and dried, obtaining a monomer represented by the following Chemical Formula 1-1b.

[Chemical Formula 1-1b]

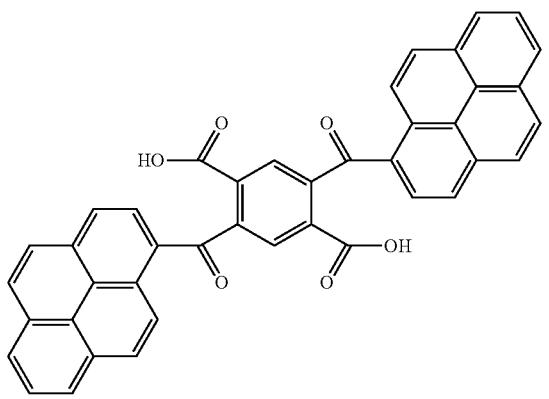

Synthesis Example 3

First Step: Coupling Reaction (Friedel-Craft Acylation)

3.3 g of pyromellitic dianhydride, 10.0 g of 1-methoxy-coronene, and 228.8 g of 1,2-dichloroethane were put in a flask and agitated. 12.1 g of aluminum chloride was slowly added to the solution, and the mixture was heated and agitated at 60° C. for 12 hours. When the reaction was complete, the reactant was added to methanol in a dropwise fashion, and a precipitate produced therein was filtered and dried.

Second Step: Demethylation Reaction 7.0 g of the compound obtained in the first step reaction, 8.1 g of 1-dodecanethiol, 2.7 g of potassium hydroxide, and 41.4 g of N,N-dimethylformamide were added in a flask and agitated at 110° C. for 8 hours. The reactant was cooled down and neutralized into a pH of about 6-7 by using a 5% hydrogen chloride solution, and a precipitate produced therein was filtered and dried, obtaining a monomer represented by the following Chemical Formula 1-2a.

[Chemical Formula 1-2a]

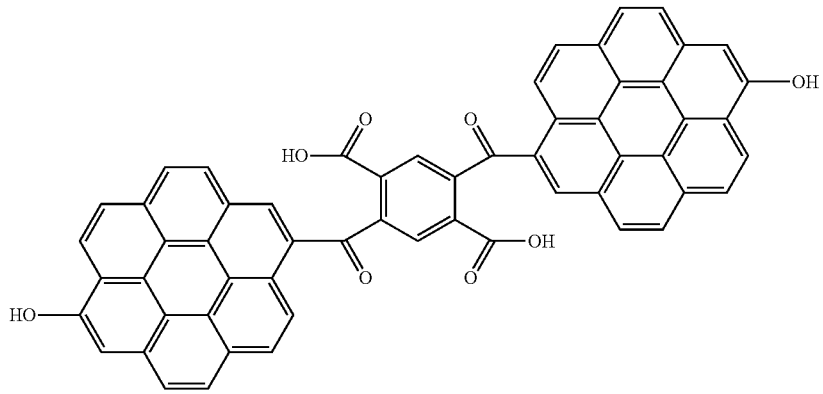

Synthesis Example 4

Coupling Reaction (Friedel-Craft Acylation)

5.45 g of pyromellitic dianhydride, 15.0 g of coronene, and 364.0 g of 1,2-dichloroethane were put in a flask and agitated. 20.0 g of aluminum chloride was slowly added to the solution, and the mixture was heated and agitated at 60° C. for 12 hours. When the reaction was complete, the reactant was added to methanol in a dropwise fashion, and a precipitate produced therein was filtered and dried, obtaining a monomer represented by the following Chemical Formula 1-2b.

[Chemical Formula 1-2b]

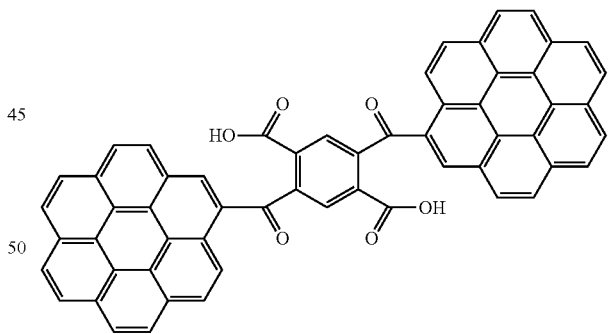

Synthesis Example 5

First Step: Coupling Reaction (Friedel-Craft Acylation)

12.67 g of perylenetetracarboxyl dianhydride, 15.0 g of 1-methoxypyrene, and 481.7 g of 1,2-dichloroethane were put in a flask and agitated. 25.85 g of aluminum chloride was slowly added to the solution, and the mixture was heated and agitated at 60° C. for 12 hours. When the reaction was complete, the reactant was added to methanol in a dropwise fashion, and a precipitate produced therein was filtered and dried.

Second Step: Demethylation Reaction 15.00 g of the compound obtained in the first step reaction, 17.3 g of 1-dodecanethiol, 5.8 g of potassium hydroxide, and 88.75 g of N,N-dimethylformamide were put in a flask and agitated at 110° C. for 8 hours. The reactant was cooled down and neutralized into a pH of about 6-7 by using a 5% hydrogen chloride solution, and a precipitate produced therein was filtered and dried, obtaining a monomer represented by the following Chemical Formula 1-3a.

diluted solution was adjusted by adding a solution of methylamylketone/methanol in a weight ratio of 4/1 having a concentration of 15 wt % thereto. This solution was put in a separatory funnel, and n-heptane was added thereto to remove a monomer having a low molecular weight, obtaining a polymer represented by the following Chemical Formula 3. The compound including an aromatic ring showed a weight average molecular weight of 2,590 and a polydispersity of 1.69.

[Chemical Formula 1-3a]

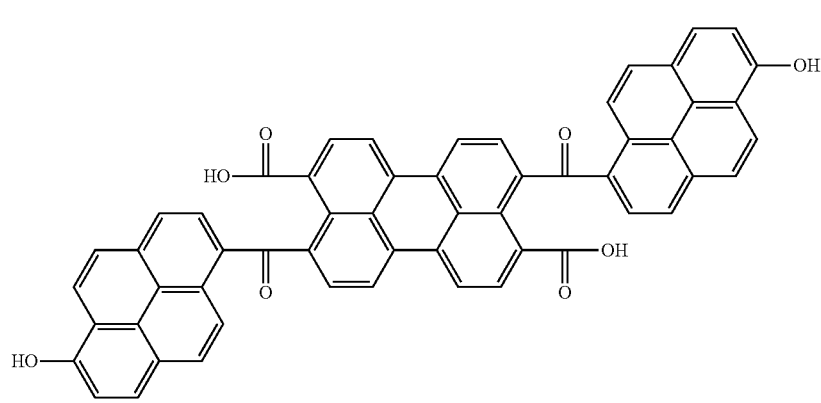

Comparative Synthesis Example 1

Coupling Reaction (Friedel-Craft Acylation)

50.0 g of coronene, 46.8 g of benzoylchloride, and 330 g of 1,2-dichloroethane were put in a flask. 44.4 g of aluminum chloride was slowly added to the solution at room temperature, and the mixture was heated up to 60° C. and agitated for 8 hours. When the reaction was complete, a precipitate produced by adding methanol to the solution was filtered and dried, obtaining a monomer represented by the following Chemical Formula 2.

[Chemical Formula 2]

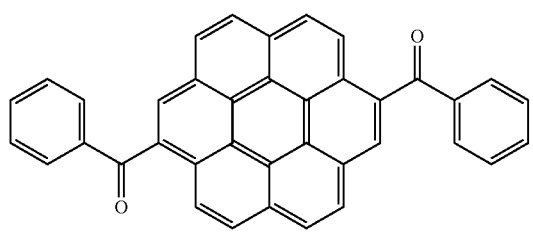

Comparative Synthesis Example 2

8.75 g of α, α'-dichloro-p-xylene, 26.66 g of aluminum chloride, and 200 g of γ-butyrolactone were put in a flask. A solution prepared by dissolving 35.03 g of 4,4'-(9-fluorenylidene)diphenol in 200 g of γ-butyrolactone was slowly added to the solution, and the mixture was agitated at 120° C. for 12 hours. After the polymerization, the reactant was concentrated after removing acid therefrom by using water. Subsequently, the polymerized product was diluted by using methylamylketone and methanol, and concentration of the

[Chemical Formula 3]

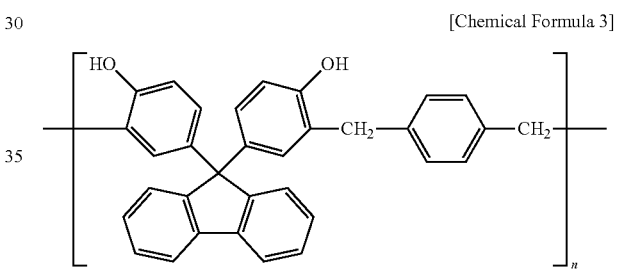

Preparation of Hardmask Composition

Examples 1 to 5

The monomers according to Synthesis Examples 1 to 5 were respectively dissolved in a mixed solvent of propylene glycol monomethyl ether acetate (PGMEA) and cyclohexanone (7:3 (v/v)) and then filtered, preparing a hardmask composition.

Comparative Examples 1 and 2

The monomer according to Comparative Synthesis Example 1 and the polymer according to Comparative Synthesis Example 2 were respectively dissolved in a mixed solvent of propylene glycol monomethyl ether acetate (PGMEA) and cyclohexanone (7:3 (v/v)) and then filtered, preparing a hardmask composition.

Evaluation 1: Evaluation of Heat Resistance 10.0 wt % of each of the hardmask compositions according to Examples 1 to 5 and Comparative Example 1 was spin-coated on a silicon wafer. The films were baked on a hot plate at 240° C. for 1 minute, and their thicknesses were measured, and then the films were baked at 400° C. for 2 minutes, and their thicknesses were measured again. Based on two thicknesses of each of the films at two temperatures, a decrease rate was calculated according to the following Calculation Equation 1 to digitize relative heat resistance of the hardmask film.

(thin film thickness after baking at 240° C.−thin film thickness after baking at 400° C.)/thin film thickness after baking at 240° C.×100(%)  [Calculation Equation 1]

The results are shown in the following Table 1.

TABLE 1

| | Thickness decrease rate of thin film (%) |
|---|---|
| Example 1 | 7.9 |
| Example 2 | 12.4 |
| Example 3 | 6.9 |
| Example 4 | 10.1 |
| Example 5 | 7.6 |
| Comparative Example 1 | 35.5 |

Referring to Table 1, the hardmask composition according to each of Examples 1 to 5 formed a hardmask layer having a thickness decrease rate and is compared with the hardmask compositions according to Comparative Example 1. The hardmask composition according to each of Examples 1 to 5 showed higher heat resistance than the hardmask composition according to Comparative Example 1.

Evaluation 2: Evaluation of Chemical Resistance 10.0 wt % of each of the hardmask compositions according to Examples 1 to 5 and Comparative Example 1 was spin-coated on a silicon wafer. The films were baked on a hot plate at 240° C. for 1 minute and cooled down at 20° C. for 1 minute. Subsequently, half of each wafer was dipped in an organic solvent mixed solution, a stripping solution, for 1 minute and dried, and then, each thickness of the dipped and non-dipped parts was respectively measured. The chemical resistance characteristic of the thin film was digitized by calculating a dissolution rate of the thin film in the organic solvent according to the following Calculation Equation 2.

(thin film thickness after baking 240° C.−thin film thickness dipped in an organic solvent mixed solution baked at 240° C.)/thin film thickness baked at 240° C.×100(%)  [Calculation Example 2]

The results are shown in the following Table 2.

TABLE 2

| | Dissolution rate of thin film (%) |
|---|---|
| Example 1 | 0.12 |
| Example 2 | 0.26 |
| Example 3 | 0.05 |
| Example 4 | 0.19 |
| Example 5 | 0.22 |
| Comparative Example 1 | 12.54 |

Referring to Table 2, the hardmask layers formed by the hardmask composition according to each of Examples 1 to 5 showed a smaller thin film dissolution rate after being dipped in the organic solvent mixed solution than a hardmask layer formed by the hardmask composition according to Comparative Example 1. Accordingly, the hardmask composition according to each of Examples 1 to 5 showed excellent chemical resistance compared with the hardmask composition according to Comparative Example 1.

Evaluation 3: Evaluation of Etch Resistance 13.0 wt % of each of the hardmask compositions according to Examples 1 to 5 and Comparative Example 2 was spin-coated on a silicon wafer and baked on a hot plate at 400° C. for 2 minutes, and the thickness of the film was measured. The thin films were respectively dry etched by using $N_2/O_2$ mixed gas for 60 seconds, and their thicknesses were measured. Subsequently, a bulk etch rate (BER) was calculated based on film thicknesses before and after etching and etching time according to Calculation Equation 3 to digitize etch resistance.

(Initial thin film thickness−thin film thickness after etching)/etching time(Å/s)  [Calculation Equation 3]

The results are shown in the following Table 3.

TABLE 3

| | Etch rate ($N_2/O_2$) |
|---|---|
| Example 1 | 24.1 |
| Example 2 | 24.5 |
| Example 3 | 22.8 |
| Example 4 | 23.9 |
| Example 5 | 23.3 |
| Comparative Example 2 | 28.9 |

Referring to Table 3, the hardmask layers formed by the hardmask composition according to each of Examples 1 to 5 showed a lower etch rate than the hardmask layer formed by the hardmask composition according to Comparative Example 2. Accordingly, the hardmask composition according to each of Examples 1 to 5 showed higher etch resistance of a thin film than the hardmask composition according to Comparative Example 2.

Evaluation 4: Evaluation of Out-Gas

The hardmask composition according to each of Examples 1 to 5 and Comparative Example 1 was spin-coated to be about 800 Å thick on a silicon wafer in which silicon nitride was prebaked at 180° C. for 60 seconds, and then, out-gas generated during the baking at 400° C. for 120 seconds was measured by using QCM (Quartz Crystal Microbalance).

The results of out-gas evaluation are shown in the following Table 4.

TABLE 4

| | Generation of out-gas |
|---|---|
| Example 1 | None |
| Example 2 | None |
| Example 3 | None |
| Example 4 | None |
| Example 5 | None |
| Comparative Example 1 | Generated during heat-treating at 400° C. |

Referring to Table 4, the hardmask composition according to each of Examples 1 to 5 showed no out-gas generated at a high temperature of 400° C. during the baking and thus, may be stably processed at a high temperature. On the contrary, the hardmask composition according to Comparative Example 1 generates relatively more out-gas and thus, may not be appropriate for a high temperature process.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A monomer for a hardmask composition, the monomer being represented by the following Chemical Formula 1:

[Chemical Formula 1]

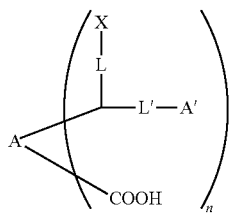

wherein, in the above Chemical Formula 1,

A and A' are each independently a substituted or unsubstituted C6 to C60 aromatic cyclic group, a substituted or unsubstituted C5 to C60 aliphatic cyclic group, a substituted or unsubstituted C2 to C60 heteroaromatic cyclic group, a substituted or unsubstituted C2 to C60 heteroaliphatic cyclic group, or a combination thereof, wherein at least one hydrogen of A' is substituted with a hydroxy group, X is a hydrogen atom, an oxygen atom, a halogen atom, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, L is a single bond or a double bond, L' is a single bond or a substituted or unsubstituted C1 to C6 alkylene group, and n is an integer ranging from 2 to 3, provided that:
when X is an oxygen atom, L is a double bond; and
when X is hydrogen, a halogen atom, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, L is a single bond, wherein the monomer is represented by the following Chemical Formula 1-1, 1-2, or 1-3:

[Chemical Formula 1-1]

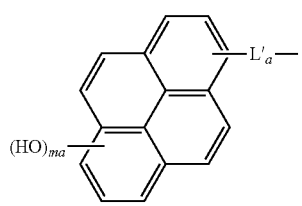

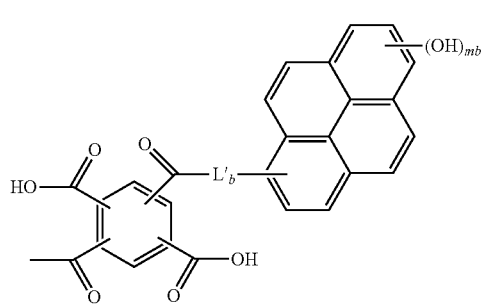

[Chemical Formula 1-2]

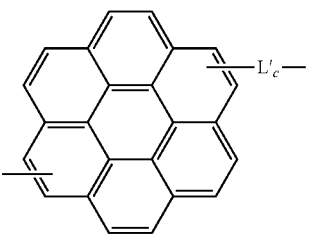

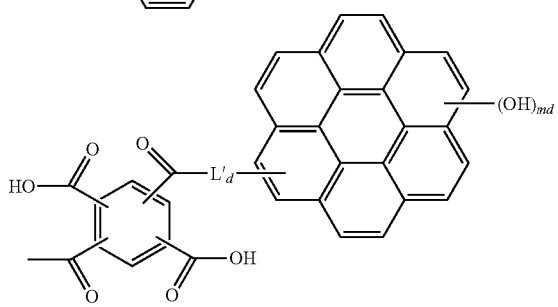

[Chemical Formula 1-3]

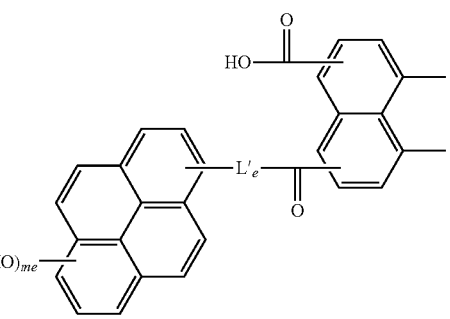

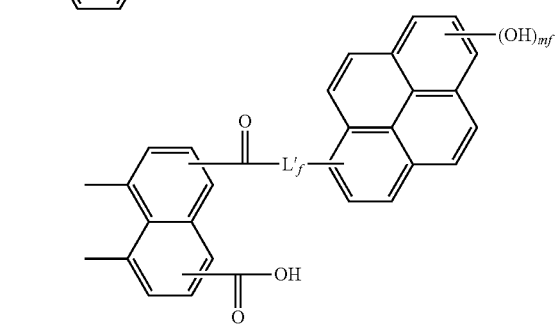

wherein, in the above Chemical Formulae 1-1, 1-2, and 1-3, $L'_a$, $L'_b$, $L'_c$, $L'_d$, $L'_e$, and $L'_f$ are each independently a single bond or a substituted or unsubstituted C1 to C6 alkylene group, ma and mb are each independently an integer of 0 to 9, provided that ma+mb is at least 1, me and mf are each independently an integer of 0 to 9, provided that me+mf is at least 1, mc and md are each independently an integer of 0 to 11, provided that mc+md is at least 1, ma, mb, mc, md, me, and mf indicate the number of a substituted hydroxy group.

2. The monomer for a hardmask composition of claim 1, wherein the monomer is represented by the following Chemical Formula 1-1a, 1-2a, or 1-3a:

[Chemical Formula 1-1a]
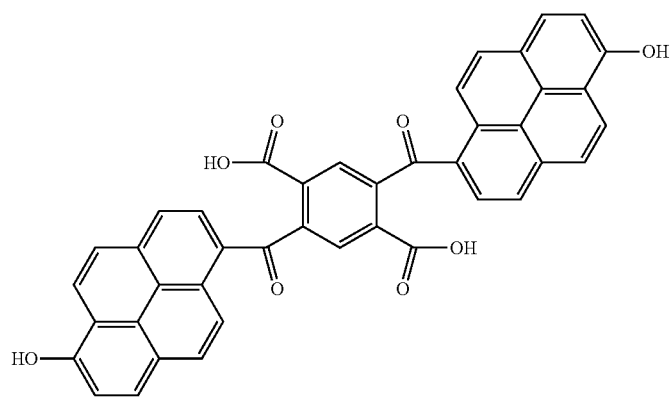
[Chemical Formula 1-2a]
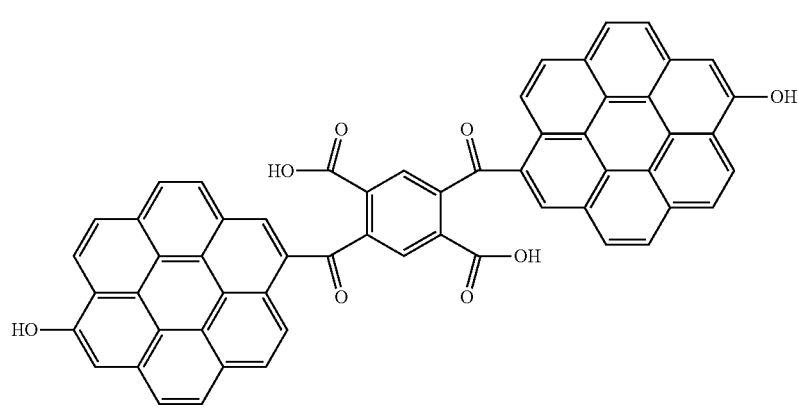
[Chemical Formula 1-3a]
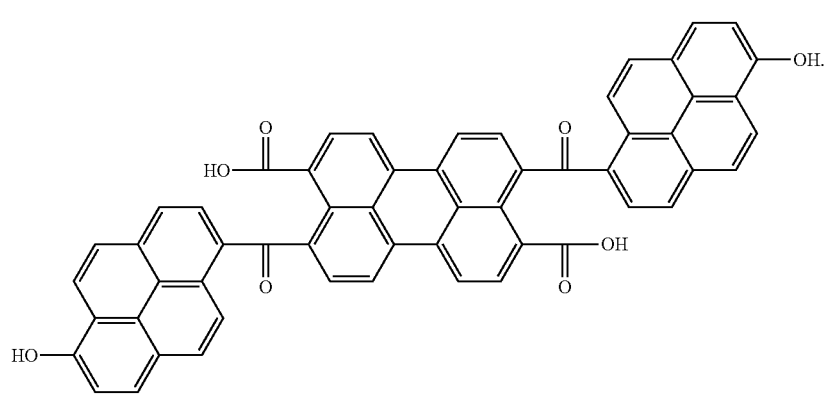
3. The monomer for a hardmask composition of claim 1, wherein the monomer has a molecular weight of 300 to 3,000.
4. A hardmask composition comprising:
a monomer represented by the following Chemical Formula 1:

[Chemical Formula 1]

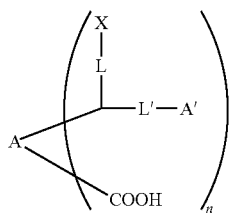

wherein, in the above Chemical Formula 1,
A and A' are each independently a substituted or unsubstituted C6 to C60 aromatic cyclic group, a substituted or unsubstituted C5 to C60 aliphatic cyclic group, a substituted or unsubstituted C2 to C60 heteroaromatic cyclic group, a substituted or unsubstituted C2 to C60 heteroaliphatic cyclic group, or a combination thereof, wherein at least one hydrogen of A' is substituted with a hydroxy group,
X is a hydrogen atom, an oxygen atom, a halogen atom, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group,
L is a single bond or a double bond,
L' is a single bond or a substituted or unsubstituted C1 to C6 alkylene group, and
n is an integer ranging from 2 to 3,
provided that:
when X is an oxygen atom, L is a double bond; and
when X is hydrogen, a halogen atom, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, L is a single bond; and
a solvent.

5. The hardmask composition of claim 4, wherein the monomer is included in an amount of 1 wt % to 30 wt % based on a total amount of the hardmask composition.

6. A method of forming patterns, comprising:
providing a material layer on a substrate;
applying the hardmask composition according to claim 4 on the material layer;
heat-treating the hardmask composition to form a hardmask layer;
forming a silicon-containing thin film on the hardmask layer;
forming a photoresist layer on the silicon-containing thin film;
exposing and developing the photoresist layer to form a photoresist pattern;
selectively removing the silicon-containing thin film and the hardmask layer using the photoresist pattern to expose a part of the material layer; and
etching an exposed part of the material layer.

7. The method of forming patterns of claim 6, wherein the hardmask composition is applied using a spin-on coating method.

8. The method of claim 6, wherein the process of forming a hardmask layer comprises heat-treating at 100° C. to 500° C.

9. A monomer for a hardmask composition, the monomer being represented by the following Chemical Formula 1:

[Chemical Formula 1]

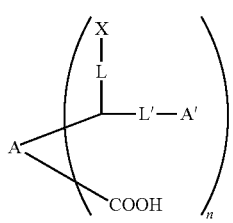

wherein, in the above Chemical Formula 1,
A is a substituted or unsubstituted C5 to C60 aliphatic cyclic group, a substituted or unsubstituted C2 to C60 heteroaromatic cyclic group, a substituted or unsubstituted C2 to C60 heteroaliphatic cyclic group, or a combination thereof,
A' is a substituted or unsubstituted C6 to C60 aromatic cyclic group, a substituted or unsubstituted C5 to C60 aliphatic cyclic group, a substituted or unsubstituted C2 to C60 heteroaromatic cyclic group, a substituted or unsubstituted C2 to C60 heteroaliphatic cyclic group, or a combination thereof,
X is a hydrogen atom, an oxygen atom, a halogen atom, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group,
L is a single bond or a double bond,
L' is a single bond or a substituted or unsubstituted C1 to C6 alkylene group, and
n is an integer ranging from 2 to 3,
provided that:
when X is an oxygen atom, L is a double bond; and
when X is hydrogen, a halogen atom, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, L is a single bond.

10. The monomer for a hardmask composition of claim 9, wherein at least one hydrogen of A' is substituted with a hydroxy group.

11. A hardmask composition comprising:
the monomer according to claim 9; and
a solvent.

12. A method of forming patterns, comprising:
providing a material layer on a substrate;
applying the hardmask composition according to claim 11 on the material layer;
heat-treating the hardmask composition to form a hardmask layer;
forming a silicon-containing thin film on the hardmask layer;
forming a photoresist layer on the silicon-containing thin film;
exposing and developing the photoresist layer to form a photoresist pattern;
selectively removing the silicon-containing thin film and the hardmask layer using the photoresist pattern to expose a part of the material layer; and
etching an exposed part of the material layer.

* * * * *